United States Patent
Malm et al.

(10) Patent No.: US 7,279,593 B2
(45) Date of Patent: Oct. 9, 2007

(54) PRIME RING SUBSTITUTED THYROID RECEPTOR ANTAGONISTS FOR THE TREATMENT OF CARDIAC AND METABOLIC DISORDERS

(75) Inventors: Johan Malm, Skogås (SE); Peter Brandt, Solna (SE); Karin Edvinsson, Stockholm (SE); Konrad Koehler, Huddinge (SE); Andrei Sanin, Vårby (SE); Sandra Gordon, Mariefred (SE)

(73) Assignee: Karo Bio AB, Huddinge (SE)

( * ) Notice: Subject to any disclaimer, the term of this patent is extended or adjusted under 35 U.S.C. 154(b) by 329 days.

(21) Appl. No.: 10/485,849

(22) PCT Filed: Aug. 13, 2002

(86) PCT No.: PCT/EP02/09120

§ 371 (c)(1),
(2), (4) Date: Dec. 15, 2004

(87) PCT Pub. No.: WO03/018515

PCT Pub. Date: Mar. 6, 2003

(65) Prior Publication Data

US 2005/0107347 A1    May 19, 2005

(30) Foreign Application Priority Data

Aug. 24, 2001 (GB) ................... 0120691.1
Apr. 3, 2002 (GB) ................... 0207719.6

(51) Int. Cl.
*C07C 69/76* (2006.01)
*A61K 31/085* (2006.01)

(52) U.S. Cl. ........................ 560/55; 560/61; 514/717

(58) Field of Classification Search ............... 560/55, 560/61; 514/717
See application file for complete search history.

(56) References Cited

FOREIGN PATENT DOCUMENTS

| EP | 0 188 351 | 7/1986 |
|----|-----------|--------|
| EP | 0580550 A1 * | 1/1994 |
| WO | 96/40048 | 12/1996 |
| WO | 99/00353 | 1/1999 |
| WO | 00/07972 | 2/2000 |
| WO | 00/39077 | 7/2000 |
| WO | 01/36365 | 5/2001 |
| WO | 01/72692 | 10/2001 |
| WO | 01/85670 | 11/2001 |

OTHER PUBLICATIONS

Leeson, P. D. et al, "Thyroid Hormone Analogues. Synthesis of 3'-Substituted 3,5-Diodo-L-thyronines and Quantitative Structure-Activity Studies of in Vitro and in Vivo Thyromimetic Activities in Rat Liver and Heart," J. Med. Chem. (1988), vol. 31, pp. 37-54.*
Pue, M.A. et al.,"The Deposition of SK and F L-94901, a Selective Thyromimetic in Rat, Dog and Cynomolgus Monkey," *European Journal of Drug Metabolism and Pharmacokinetics*, vol. 14, No. 3, pp. 209-219 (1989).
Leeson, Paul et al., "Thryoid Hormone Analogues. Synthesis of 3'-Substituted 3,5-Diiodo-L-thyronines and Quantitative Structure-Activity Studies of in Vitro and in Vivo Thyromimetic Activities in Rat Liver and Heart," *J. Med. Chem.*, vol. 37, No. 1, pp. 37-54 (1988).
Leeson, Paul et al., "Synthesis of Thyroid Hormone Analogs. Part 1. Preparation of 3'-heteroarylmethyl-3,5-diiodo-L-thyronines Via Phenol-dinitrophenol Condensation and Relationships Between Structure and Selective Thyromimetic Activity," *J. of the Chem. Soc 'y*, vol. 12 pp. 3085-3096 (1988).

* cited by examiner

*Primary Examiner*—Joseph K. McKane
*Assistant Examiner*—Janet L. Coppins
(74) *Attorney, Agent, or Firm*—Wiggin and Dana LLP; Todd E. Garabedian; Elizabeth A. Galletta

(57) ABSTRACT

This invention relates to novel compounds which are thyroid receptor ligands, preferably antagonists, and to methods for using such compounds in the treatment of cardiac and metabolic disorders, such as cardiac arrhythmias, thyrotoxicosis, subclinical hyperthyrodism and liver diseases.

8 Claims, No Drawings

PRIME RING SUBSTITUTED THYROID RECEPTOR ANTAGONISTS FOR THE TREATMENT OF CARDIAC AND METABOLIC DISORDERS

FIELD OF THE INVENTION

This invention relates to novel compounds which are thyroid receptor ligands, preferably antagonists, and to methods for using such compounds in the treatment of cardiac and metabolic disorders, such as cardiac arrhythmias, thyrotoxicosis, subclinical hyperthyrodism and liver diseases.

BACKGROUND OF THE INVENTION

Nuclear hormone receptors comprise a class of intracellular, mostly ligand-regulated transcription factors, which include receptors for thyroid hormones. Thyroid hormones exert profound effects on growth, development and homeostasis in mammals. They regulate important genes in intestinal, skeletal and cardiac muscles, liver and the central nervous system, and influence the overall metabolic rate, cholesterol and triglyceride levels, heart rate, and affect mood and overall sense of well being.

There are two major subtypes of the thyroid hormone receptor, TRα and TRβ, expressed from two different genes. Differential RNA processing results in the formation of at least two isoforms from each gene. The $TR\alpha_1$, $TR\beta_1$ and $TR\beta2$ isoforms bind thyroid hormone and act as ligand-regulated transcription factors. The $TR\alpha_2$ isoform is prevalent in the pituitary and other parts of the central nervous system, does not bind thyroid hormones, and acts in many contexts as a transcriptional repressor. In adults, the $TR\beta_1$ isoform is the most prevalent form in most tissues, especially in the liver and muscle. The $TR\alpha_1$ isoform is also widely distributed, although its levels are generally lower than those of the $TRP\beta_1$ isoform. A growing body of data suggest that many or most effects of thyroid hormones on the heart, and in particular on the heart rate and rhythm, are mediated through the $TR\alpha_1$ isoform, whereas most actions of the hormones on the liver, muscle and other tissues are mediated more through the β-forms of the receptor. It is believed that the α-isoform of the receptor is the major influence on heart rate for the following reasons: (i) tachycardia is very common in the syndrome of generalized resistance to thyroid hormone in which there are defective TRβ-isoforms, and consequently high circulating levels of $T_4$ and $T_3$; (ii) Tachycardia was observed in the only described patient with a double deletion of the TRβ gene (Talceda et al, *J. Clin. Endrocrinol. & Metab.* 1992, 74, 49); (iii) a double knockout TRα gene (but not β-gene) in mice showed bradycardia and lengthening of action potential compared to control mice (Functions of Thyroid Hormone Receptors in Mice: D. Forrest and B. Vennström, Thyroid, 2000, 10, 41-52); (iv) western blot analysis of human myocardial TRs show presence of the $TR\alpha_1$, $TR\alpha_2$ and $TR\beta_2$ proteins, but not $TR\beta_1$.

If the indications above are correct, an a-selective thyroid hormone receptor antagonist that interacts selectively with the heart would offer an attractive alternative treatment of heart related disorders, such as atrial and ventricular arrhythmias.

Atrial fibrillation (AF) is the most common type of sustained arrhythmia encountered in primary care practice and is significantly more common in elderly patients, thus reflecting a reduction in the threshold for AF with age.

Pharmacological treatment of AF involves the following types of anti-arrhythmic drugs according to Vaughan-Williams classification: (i) of class I such as disopyramide and flecainide (sodium channel blockers); (ii) of class III such as amiodarone (potassium channel blocker, prolongation of repolarization); (iii) of class IV such as verapamil and dilitazem (calcium channel blockers). Many patients are also subjected to electric cardioversions in order to convert atrial fibrillation into sinus rhythm. It should be noted that current therapies are associated with pro-arrhythmic risks and anti-arrhythmic agents often have insufficient efficacy partly because effective doses are limited by side-effects.

Ventricular arrhythmia, especially sustained ventricular tachycardia (VT) and ventricular fibrillation (VF), is the main cause of death associated with heart attack. Historically, three types of antiarrhythmic agents, class I agents, β-adrenergic blockers (class II), amiodarone and sotalol, appeared to offer the best scope for mortality reduction in patients with cardiac disease by preventing the occurrence of VT/VF.

The outcome of CAST (Cardiac Arrhythmia Supression Trial, *N. Engl. J. Med.*, 321 (1989) 406-412) and its successor SWORD (Survival With Oral D-sotatol trial, 1994) created much concern regarding the potential of class I agents and sotalol. It was found that class I agents did not decrease mortalities in patient groups at risk for sudden cardiac death. For some subsets of patients, class I agents even proved to increase mortality. The SWORD trial was stopped when sotalol proved to be associated with higher death rate in patients, than the placebo. A consequence of these results is that the use of implantable defibrillators and surgical ablation have increased and that the trend in the industry has been towards the development of highly specific class III agents. Some of these channel blockers have been withdrawn from clinical development due to proarrhythmic effects and the subject remains under intensive debate. In this context it should be noted that amiodarone, despite its complex pharmacokinetics, mode of action (amiodarone is not regarded as a pure class III agent) and numerous side effects, is currently considered by many to be the most effective agent in the control of both atrial and ventricular arrhythmia.

Thyrotoxicosis is the clinical syndrome that results when tissues are exposed to elevated levels of circulating thyroid hormones, thyroxine (3,5,3',5'-tetraiodo-L-thyronine, or $T_4$) and triiodothyronine (3,5,3'-triiodo-L-thyronine, or $T_3$). Clinically, this state often manifests itself in weight loss, hypermetabolism, lowering of serum LDL levels, cardiac arrhythmia, heart failure, muscle weakness, bone loss in postmenopausal women, and anxiety. In most instances, thyrotoxicosis is due to hyperthyroidism, a term reserved for disorders characterized by overproduction of thyroid hormones by the thyroid gland. The ideal treatment of hyperthyroidism would be the elimination of its cause. This is however not possible in the more common diseases producing thyroid hypersecretion. At present, treatment of hyperthyroidism is directed to reducing overproduction of thyroid hormones by inhibiting their synthesis or release, or by ablating thyroid tissue with surgery or radioiodine.

Drugs inhibiting thyroid hormone synthesis, release, or peripheral conversion of $T_4$ to $T_3$ include antithyroid drugs (thionamides), iodide, iodinated contrast agents, potassium perchlorate and glucocorticoids. The main action of antithyroid drugs such as methimazole (MMI), carbimazole, and propylthiouracil (PTU), is to inhibit the organification of iodide and coupling of iodotyrosines, thus blocking the synthesis of thyroid hormones. As they neither inhibit iodide transport nor block the release of stored thyroid hormones, control of hyperthyroidism is not immediate and in most cases requires 2 to 6 weeks. Factors that determine the speed of restoration of euthyroidism include disease activity, initial levels of circulating thyroid hormones, and intrathyroidal hormone stores. Serious side effects are not common with antithyroid drugs. Agranulocytosis is the most feared problem and has been observed with both MMI or PTU treatment. Elderly persons may be more susceptible to this side effect, but agranulocytosis can occur in younger age groups, although less frequently. Inorganic iodide given in pharmacological doses (as Lugol's solution or as saturated solution of potassium iodide, SSKI) decreases its own transport into the thyroid, thus inhibiting iodide organification (the Wolff-Chaikoff effect), and rapidly blocks the release of $T_4$ and $T_3$ from the gland. However, after a few days or weeks, its antithyroid action is lost, and thyrotoxicosis recurs or may worsen. Short-term iodide therapy is used to prepare patients for surgery, usually in combination with a thionamide drug. Iodide is also used in the management of severe thyrotoxicosis (thyroid storm), because of its ability to inhibit thyroid hormone release acutely. Perchlorate interferes with accumulation of iodide by the thyroid. Gastric irritation and toxic reactions limit the long-term use of perchlorate in the management of hyperthyroidism. Glucocorticoids in high doses inhibit the peripheral conversion of $T_4$ to $T_3$. In Graves' hyperthyroidism, glucocorticoids appear to decrease $T_4$ secretion by the thyroid, but the efficiency and duration of this effect is unknown. The aim of surgical treatment or radioiodine therapy of hyperthyroidism is to reduce the excessive secretion of thyroid hormones by removal or destruction of thyroid tissue. Subtotal or near-total thyroidectomy is performed in Graves' disease and toxic multinodular goiter. Restoration of euthyroidism before surgery is mandatory. The classical approach combines a course of thionamide treatment to restore and maintain euthyroidism, and the preoperative administration of iodide for approximately 10 days in order to induce involution of the gland. Propranolol and other beta-adrenergic antagonist drugs are useful in controlling tachycardia and other symptoms of sympathetic activation.

A high affinity ThR antagonist would in principle have the ability to restore euthyrodism quicker than any of the above agents, considered that its action is competitive for the ThR receptor. Such an agent could be used either alone or in combination with the above drugs, or alternatively before an ablative treatment. It may also serve as a safer substitute for antithyroid drugs, especially in elderly patients at a high risk of agranulocytosis. Furthermore, hyperthyrodism can aggravate pre-existing heart disease and also lead to atrial fibrillation (AF), congestive heart failure, or worsening of angina pectoris. In the elderly patient, often with mild but prolonged elevation of plasma thyroid hormones, symptoms and signs of heart failure and complicating AF may dominate the clinical picture and mask the more classical endocrine manifestations of the disease.

DESCRIPTION OF THE INVENTION

In accordance with the present invention, compounds are provided which are thyroid receptor ligands, having the general formula I:

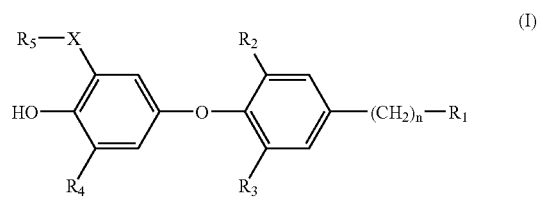

or a pharmaceutically acceptable salt thereof, wherein:
$R_1$ is independently selected from: carboxylic acid (—$CO_2H$); carboxylic acid esters (—$CO_2R^c$); alpha-hydroxy carboxylic acid (—$CH(OH)CO_2H$); alpha-amino carboxylic acid (—$CH(NH_2)CO_2H$); phosphonic acid (—$PO(OH)_2$); phosphamic acid (—$PO(OH)NH_2$); sulphonic acid (—$SO_2OH$); hydroxamic acid (—CONHOH); oxamic acid (—$NHCOCO_2H$); and malonamic acid (—$NHCOCH_2CO_2H$), or bioisosteric equivalents of any of these groups;
$R_2$ and $R_3$ are the same or different and independently selected from: chlorine; bromine; iodine; $C_{1-4}$ alkyl; $C_{2-4}$ alkenyl; $C_{2-4}$ alkynyl, each being optionally substituted with 1, 2 or 3 halogen atoms which may be the same or different, or a bioisosteric equivalent of any thereof;
R is selected from: halogen; $C_{1-4}$ alkyl; $C_{2-4}$ alkenyl; and $C_{2-4}$ alkynyl, each being optionally substituted with 1, 2 or 3 halogen atoms which may be the same or different, or a bioisosteric equivalent of any therof;
X is selected from: —$CH_2$—$CH_2$—; —$CH_2$—$CH_2$—$CH_2$; —CH=CH—; —CH=CH—$CH_2$—; —C≡C—; and —C≡C—$CH_2$;
$R_5$ is selected from: $C_{6-10}$ aryl; $C_{1-9}$ heteroaryl; and $C_{5-10}$ cycloalkyl, each being optionally substituted with 1, 2, or 3 groups $R^b$ which may be the same or different;
$R^b$ is selected from: halogen; —CN; —$CO_2H$; —CHO; —$NO_2$; $C_{1-4}$ alkyl; $C_{2-4}$ alkenyl; $C_{2-4}$ alkynyl; $C_{1-4}$ alkoxy; $C_{2-4}$ alkenoxy; $C_{2-4}$ alkynoxy; $C_{1-4}$ alkylthio; $C_{2-4}$ alkenylthio; $C_{2-4}$ alkynylthio; —$(CH_2)_n$—OH; —$(CH_2)_n$—$O(C_{1-4})$; —$(CH_2)_n$—$NH_2$; —$(CH_2)_n$—$NH(C_{1-4})$; and —$(CH_2)_n$—$N(C_{1-4})_2$, or a bioisosteric equivalent of any therof;
$R^c$ is selected from: $C_{1-4}$ alkyl or haloalkyl; $C_{2-4}$ alkenyl or haloalkenyl; and $C_{2-4}$ alkynyl haloalkynyl;
n is 0, 1 or 2;

included for the variables above are all possible stereoisomers; prodrug ester forms; and radioactive forms thereof.

DETAILED DESCRIPTION OF THE INVENTION

The following definitions apply to the terms as used throughout this specification, unless otherwise limited in specific instances.

The term "thyroid receptor ligand" as used herein is intended to cover any chemical substance which binds to a thyroid receptor. The ligand may act as an antagonist, an agonist, a partial antagonist or a partial agonist.

The term "alkyl" as employed herein alone or as part of another group refers to an acyclic straight or branched chain radical, containing 1 to 4 carbons, such as methyl, ethyl, propyl, propyl, n-butyl replaced by halogens. When $R_2$ and $R_3$ is selected from alkyl and substituted by halogen, the preferred groups are —$CF_3$, —$CHF_2$ and —$CH_2F$. Where alkyl is substituted with halogen to give haloalkyl, preferably 1 to 3 of the hydrogen atoms are replaced.

The term "alkenyl" as used herein by itself or as part of another group refers to straight or branched chain radicals of 2 to 4 carbons and at least one carbon-to-carbon double bond Preferably one carbon-to-carbon double bond is present. Examples of normal chain radicals are ethenyl, propenyl, butenyl and the like. As described above with respect to the "alkyl", the straight or branched portion of the alkenyl group may be substituted by halogen.

The term "alkynyl" as used herein by itself or as part of another group refers to straight or branched chain radicals of 2 to 4 carbons and at least one carbon-to-carbon triple bond. Preferably one carbon-to-carbon triple bond is present. Examples of normal chain radicals are ethynyl, propynyl, butynyl and the like. As described above with respect to the "alkyl", the straight or branched portion of the alkenyl group may be substituted by halogen when a substituted alkynyl group is provided.

The term "cycloalkyl" as employed herein alone or as part of another group refers to saturated cyclic hydrocarbon groups or partially unsaturated cyclic hydrocarbon groups, independently containing 1 to 2 carbon to carbon double bonds or carbon to carbon triple bonds. The cyclic hydrocarbon contains 5 to 10 carbons, including rings that are fused. Preferred cycloalkyl groups include 5 to 7 carbons, such as cyclopentyl, cyclohexyl, cycloheptyl, which may be optionally substituted through available carbons with 1 to 3 groups selected from $R^b$, which groups may be the same or different It should be understood that the present invention also involves cycloalkyl rings where 1 to 2 carbons in the ring are replaced by either —O—, —S— or —N—, thus forming a saturated or partially saturated heterocycle. Examples of such rings are piperidine, piperazine, morpholine, thiomorpholine, pyrrolidine, oxazolidine, thiazolidine, tetrahydrofurane, and tetrahydrothiophene. Preferred heterocyclic rings are 5- or 6-membered, which may be optionally substituted through available carbons as in the case of "aryl" and "heteroaryl".

The term "aryl" as employed herein alone or as part of another group refers to monocyclic or bicyclic aromatic groups, consisting of 6 to 10 carbons in the ring portion, including partially saturated rings as indanyl and tetrahydronaphthyl. The preferred aryl group is phenyl, which may be substituted with 1 to 3 groups selected from $R^b$ which may be the same or different.

The term "halogen" as used herein refers to fluorine, chlorine, bromine and iodine. When halogen is selected for $R_3$ and/or $R_4$ the preferred halogen group is bromine.

The term "alkoxy" refers to those groups of the designated carbon length in either a straight or branched configuration attached through an oxygen linkage and if two or more carbons in length, they may incude a, double or a triple bond. Examples of such alkoxy groups are methoxy, ethoxy, propoxy, allyloxy, propargyloxy, butoxy, tert-butoxy, and the like. Alkoxy also refers to a radical where 1 to 3 hydrogens can be replaced by fluorine through the available carbons. When alkoxy is selected and substituted by halogen, the preferred groups are —OCF$_3$, —OCHF$_2$ and —OCH$_2$F.

The term "thio" as used herein as a part of another group, exemplified by "alkylthio", refers to a carbon-sulphur-carbon bond and if two or more carbons in length may incude a double or a triple bond. The term "thio" may also include higher oxidation states of sulphur, such as sulfoxides —SO— and sulphones —SO$_2$—. "Alkylthio" also refer to a radical where 1 to 3 hydrogens can be replaced by halogens through the available carbons. When alkylthio is substituted by halogen, the preferred groups are —SCF$_3$, —SCHF$_2$ and —SCH$_2$F.

The term "heteroaryl" as used herein alone or as a part of another group refers to a group containing 1 to 9 carbon atoms, where the aromatic ring includes 1 to 4 heteroatoms, as nitrogen, oxygen or sulfur. Such rings may be fused to another aryl or heteroaryl ring, and include possible N-oxides. The heteroaryl group may optionally be substituted by the available carbons with 1 to 3 substituents $R^b$ which may be the same or different.

The term "phosphonic acid" and "phosphamic acid" refers to phosphorus-containing groups of the structures:

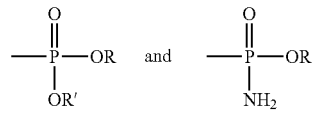

wherein R and R' are independently selected from hydrogen, $C_{1-4}$ alkyl, $C_{2-4}$ alkenyl or $C_{2-4}$ alkynyl.

The terms radical "—N(C$_{1-4}$)$_2$" and "—NH(C$_{1-4}$)" refer respectively to secondary or tertiary amines where "C" is equal to 1, 2, 3, or 4 carbons in a branched or straight chain. Groups covered by the above definition include: —N(C$_{1-4}$ alkyl)$_2$, —NH(C$_{1-4}$ alkyl), —N(C$_{2-4}$ alkenyl)$_2$, —NH(C$_{2-4}$ alkenyl), —N(C$_{2-4}$ alkynyl)$_2$, —NH(C$_{2-4}$ alkynyl), —N(C$_{1-4}$ alkyl)(C$_{2-4}$ alkenyl), —N(C$_{2-4}$ alkyl)(C$_{2-4}$ alkynyl), and —N(C$_{2-4}$ alkenyl)(C$_{2-4}$ alkynyl).

Likewise the term "—O(C$_{1-4}$)" refers to an alkoxy group where "C" is equal to 1, 2, 3, or 4 carbons in a branched or straight chain. Groups covered by the above definition include: —O(C$_{1-4}$ alkyl), —O(C$_{2-4}$ alkenyl), and —O(C$_{2-4}$ alkynyl).

The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience: New York, 1970, 64-80; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark R D, Ferguson A M, Cramer R D, "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity", *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J, "Bioisosteric approach in the design of new dopaminergic/serotonergic ligands", *Curr. Med. Chem.* 1998, 5, 493-512 (x) Thornber C W, "Isosterism and molecular modification in drug design", *Chem. Soc. Rev.* 1979, 8, 563-80.

The compounds of formula I can be present in the form of salts, in particular pharmaceutically acceptable salts. A compound having at least one acid group (for example —COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or trilower alylamine, for example ethyl, tertbutyl, diethyl, diisopropyl, triethyl, tributyl or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included. Preferred salts of the compounds of formula I which include an acid group include sodium, potassium and magnesium salts and pharmaceutically acceptable organic amines.

The compounds of formula I having at least one basic center (for example —NH— in piperidine) can also form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additional basic center. Salts which are unsuitable for pharmaceutical uses but which can be employed, for example, for the isolation or purification of free compounds I or their pharmaceutically acceptable salts, are also included. Preferred salts of the compounds of formula I which include a basic group include monohydrochloride, hydrogensulfate, methanesulfonate, phosphate or nitrate.

An acid center (for example —COOH) in formula I can form "prodrug ester forms" known in the art such as pivaloyloxymethyl or dioxolenylmethyl. Such prodrug esters are described in standard references such as Chapter 31, written by Camille G. Wermuth et al., in "The Practice of Medicinal Chemistry", ed. C. G. Wermuth, Academic Press, 1996 (and the references contained therein).

Compounds of the invention can be stereoisomers, which have one or more asymmetric centers and can exist in the form of racemates, single enantiomers, individual diastereomers, with all possible isomers, and mixtures thereof, all of which are within the scope of the invention.

In one embodiment of the present invention there is provided compounds according to formula I, wherein $R_1$ is selected from: carboxylic acid (—$CO_2H$); alpha-hydroxy carboxylic acid (—CH(OH)$CO_2H$); and alpha-amino carboxylic acid (—CH($NH_2$)$CO_2H$).

In another embodiment of the present invention there are provided compounds according to formula I, wherein $R_3$ is bromine.

In yet another embodiment of the present invention there are provided compounds according to formula I, wherein $R_4$ is isopropyl.

In yet another embodiment of the present invention there are provided compounds according to formula I, wherein $R_5$ is $C_6$ aryl or $C_{1-5}$ heteroaryl.

In yet another embodiment of the present invention there are provided compounds according to formula I, wherein $R_1$ is a carboxylic acid (—$CO_2H$) and X is —C=C—.

In a preferred embodiment of the present invention there are provided compounds according to formula I, wherein $R_1$ is a carboxylic acid (—$CO_2H$); $R_2$ and $R_3$ is bromine; $R_4$ is isopropyl; $R_5$ is $C_6$ aryl or $C_{1-5}$ heteroaryl.

Particularly preferred compounds according to formula I include:
3,5-dibromo-4-[4-hydroxy-3-isopropyl-5-((E)-styryl)phenoxy]benzoic acid (E1);
3-{3,5-dibromo-4-[4-hydroxy-3-isopropyl-5-((E)-styryl)phenoxy]phenyl}propionic acid (E2);
3-{3,5-dibromo-4-[4-hydroxy-3-isopropyl-5-((E)-2-pyridin-4-yl-vinyl)phenoxy]-phenyl}-propionic acid (E3);
3-{3,5-dibromo-4-[4-hydroxy-3-isopropyl-5-((E)-2-pyridin-2-yl-vinyl)phenoxy]phenyl{-propionic acid (E4);
3-{3,5-dibromo-4-[4-hydroxy-3-isopropyl-5-((E)-2-pyrazine-2-yl-vinyl)phenoxy]phenyl}-propionic acid (E5);
3-(3,5-dibromo-4-{3-[(E)-2-(4-dimethylaminomethylphenyl)vinyl]4-hydroxy-5-isopropylp phenyl)propionic acid (E6);
3-(3,5-Dibromo-4-{4-hydroxy-3-isopropyl-5-[(E)-2-(4-methylthiazol-5-yl)vinyl]phenoxy}-phenyl)propionic acid (E7);
4-((E)-2-{5-[2,6-Dibromo-4-(2-carboxyethyl)phenoxy]-2-hydroxy-3-isopropylphenylvinyl)-benzoic acid (E8);
3-{3,5-Dibromo-4-[4-hydroxy-3-isopropyl-5-(2-pyridin-4-yl-ethyl)-phenoxy]-phenyl}propionic acid (E9);
3-[3,5-Dibromo-4-(4-hydroxy-3-isopropyl-5-phenetyl-phenoxy)-phenyl]-propionic acid (E10);
3-[3,5-Dibromo-4-[4-hydroxy-3-isopropyl-5(E)-styryl-phenoxy)phenyl]-2-hydroxyl propionic acid (E11);
3-{3,5-Dibromo-4-[4-hydroxy-3-isopropyl-5-((E)-2-pyridin-4-yl-vinyl)-phenoxy]-phenyl}-2-hydroxy propionic acid (E12);
3-[3,5-Dibromo-4-(4-hydroxy-3-isopropyl-5-phenylethyl-phenoxy)-phenyl]-2-hydroxy-propionic acid (E13);
3-{3,5-Dibromo-4-[4-hydroxy-3-isopropyl-5-(2-pyridin-4-yl-ethyl)-phenoxy]-phenyl}-2-hydroxy propionic acid (E14).

and pharmaceutically acceptable salts and stereoisomers thereof.

The compounds of the invention are thyroid receptor antagonists or partial agonists, preferably α-selective. As such they are useful in medical therapy. Furthermore, they are useful in the prevention, inhibition or treatment of a disease which is dependent on the expression of a $T_3$ regulated gene or associated with metabolic dysfunction. Examples of such diseases are heart related disorders, such as cardiac arrhythmias (atrial and ventricular arrhythmias), especially atrial fibrillation and ventricular tachycardia and fibrillation. The compounds of the invention may also be useful for the treatment of thyrotoxicosis, especially in the therapy of elderly patients, subclinical hyperthyroidism, and other endocrine disorders related to thyroid hormone.

Compounds of the invention may also be $T_3$ antagonists with a preferential hepatic activity, and such may be used for medical treatment to improve the clinical course of various liver diseases such as: alcoholic liver disease, viral (hepatitis A, B, C, D, E) liver diseases, and immunological liver diseases. The $T_3$-antagonist may have principal activity in the liver, and thus have preferential hepatic activity, and with minimal activity in the rest of the body to reduce side-effects associated with the treatment. It is known that induction of a state with abnormally low levels of circulating thyroid hormones (hypothyroidism) is a rewarding treatment of liver diseases such as hepatic cirrhosis/fibrosis. Nevertheless, induction of hypothyroidism is not an accepted therapy for liver diseases. The major reason is that currently available methods to induce hypothyroidism inevitably leads to a general hypothyroid state since the production of T4 by the thyroid is blocked. General, systemic hypothyroidism causes a number of unacceptable clinical symptoms such as myxedema, depression, constipation etc. Also, the time of onset from initiation of therapy until hypothyroidism is manifest is rather long, typically several months. T3-receptor antagonists also induce hypothyroidism but much faster than standard therapies. A T3-receptor antagonist with major accumulation in the liver does spare the body from the deleterious impact of general hypothyroidism. The compounds of the invention may therefore be used to treat certain liver diseases, such as chronic alcoholism, acute hepatitis, chronic hepatitis, hepatitis C-induced liver cirrhosis, and liver fibrosis.

The compounds of the invention may also be used to treat certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

The invention includes pharmaceutical compositions comprising one or more of the compounds described above and a pharmaceutically acceptable carrier, as well as a process for making a pharmaceutical composition comprising combining any of the compounds described above and a pharmaceutically acceptable carrier.

Another embodiment of the invention is a method of treating, inhibiting or preventing a disease which is dependent on the expression of a $T_3$ regulated gene or associated with metabolic dysfunction in a mammal in need thereof by administering to the mammal a therapeutically effective amount of any of the compounds or pharmaceutical compositions described above. The said diseases may be heart related disorders, such as cardiac arrhythmias (atrial and ventricular arrhythmias), especially atrial fibrillation and ventricular tachycardia and fibrillation, especially in elderly patients, subclinical hyperthyroidism, and other endocrine disorders related to thyroid hormone.

The invention further includes a method of treating, inhibiting or preventing certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

The invention includes the use of any of the compounds described above in the preparation of a medicament for the treatment, inhibition or prevention of a disease dependent on the expression of a $T_3$ regulated gene or associated with metabolic dysfunction. Still further included in the invention is the use of any of the compounds described above in the preparation of a medicament for the treatment and/or prevention of heart related disorders, such as cardiac arrhytmias (atrial and ventricular arrhythmias), especially atrial fibrillation and ventricular tachycardia and fibrillation, especially in elderly patients, subclinical hyperthyroidism, and other endocrine disorder related to thyroid hormone.

Further exemplifying the invention is the use of any of the compounds described above in the preparation of a medicament for the treatment, inhibition or prevention of certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

The compounds of the present invention can be administered in oral dosage forms such as tablets, capsules (each of which includes sustained release or timed release formulations), pills, powder, granules, elixirs, tinctures, suspensions, syrups and emulsions. Likewise, they may also be administered in intravenous form (bolus or infusion), intraperitoneal, topical (e.g., ocular eyedrop), subcutaneous, intramuscular, or transdermal (e.g., patch) all using techniques well known to those of ordinary skill in the pharmaceutical arts.

The dosage regimen utilizing the compounds of the present invention is selected in accordance with a variety of factors including type, species, age, weight, sex, and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, combat or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, or 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute for a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include without limitation starch, methylcellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed form a variety of phospholipids, such as cholesterol, stearylamine or phosphatidylcholines.

The present invention includes within its scope prodrugs of the compounds of this invention. In general, such prodrugs will be functional derivatives of the compounds of this invention which are readily convertible in vivo into the required compounds. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example in "Design of Prodrugs" ed. H. Bundgaard, Elsevier, 1985. Metabolites of the compounds include active species produced upon introduction of compounds of this invention into the biological milieu.

The compounds of formula I may for example be prepared by the processes described in the following schemes. Examples of reagents and procedures for these reactions appear hereinafter and in the following Examples. Those skilled in the art will readily understand that the conditions and processes described in the following preparative procedures can be varied. The compounds of the present invention can be prepared according to the general methods outlined in the schemes below, and according to the methods described. All temperatures are in degrees Celcius unless otherwise noted. The following abbreviations used herein are explained as follows: 20-25° C. (room temperature, r.t.); molar equivalent (equiv.); dimethyl formamide (DMF); ethyl acetate (EtOAc); tetrahydrofuran (THF); solid phase extraction (SPE), electrospray mass spectroscopy (ES/MS).

In Step 1, ether 1 is regioselectively nitrated employing nitric acid in benzene at room temperature to give compound 2. Compound 2 is then reduced in Step 2 to provide derivative 3. Diazotation of Compound 3 affords derivative 4. Removal of the alkyl group $R_6$ of compound 4 in Step 4 provides derivative 5, which can undergo palladium-catalyzed cross coupling to yield Compound 6 in Step 5.

When X in formula I is a saturated alkyl chain, hydrogenation of derivative 6 affords compound 8. Alternatively, derivative 4 can undergo palladium-catalyzed cross coupling in Step 5 to yield compound 7. In Step 4 removal of the alkyl group $R_6$ of derivative 7 provides compound 6. This alternative procedure is described in SCHEME II.

Hydrolysis of the corresponding alkyl ester yields the alkyl acid derivative when $R_1$ of formula I is carboxylic acid (—$CO_2H$); alpha-hydroxy carboxylic acid (—CH(OH)$CO_2H$); alpha-amino carboxylic acid (—CH($NH_2$)$CO_2H$); sulphonic acid (—$SO_2OH$); oxamic acid (—NHCOCO$_2H$); or malonamic acid (—NHCOCH$_2CO_2H$).

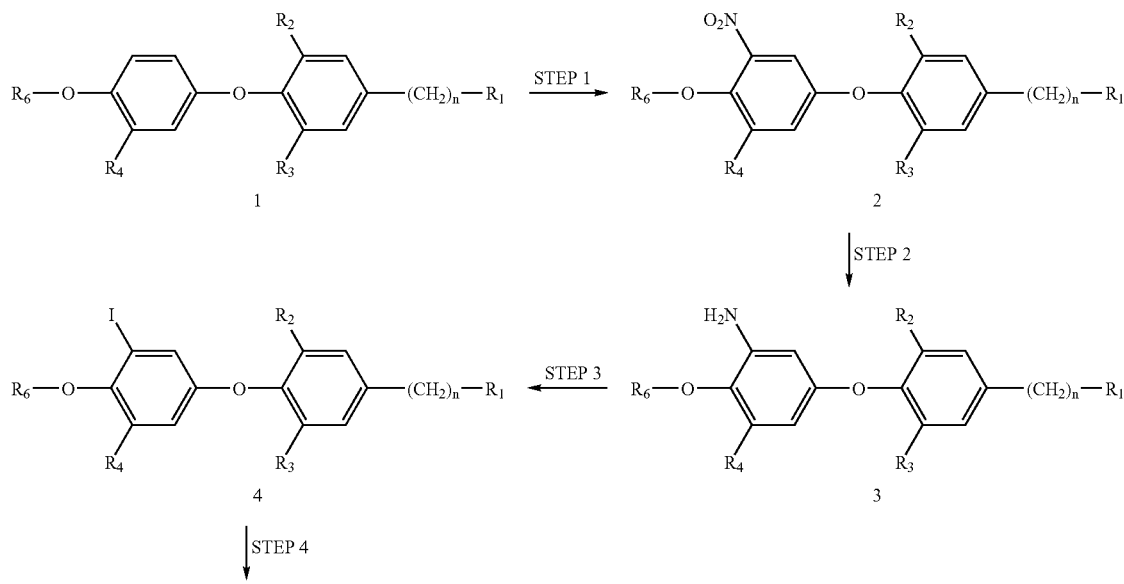

SCHEME I

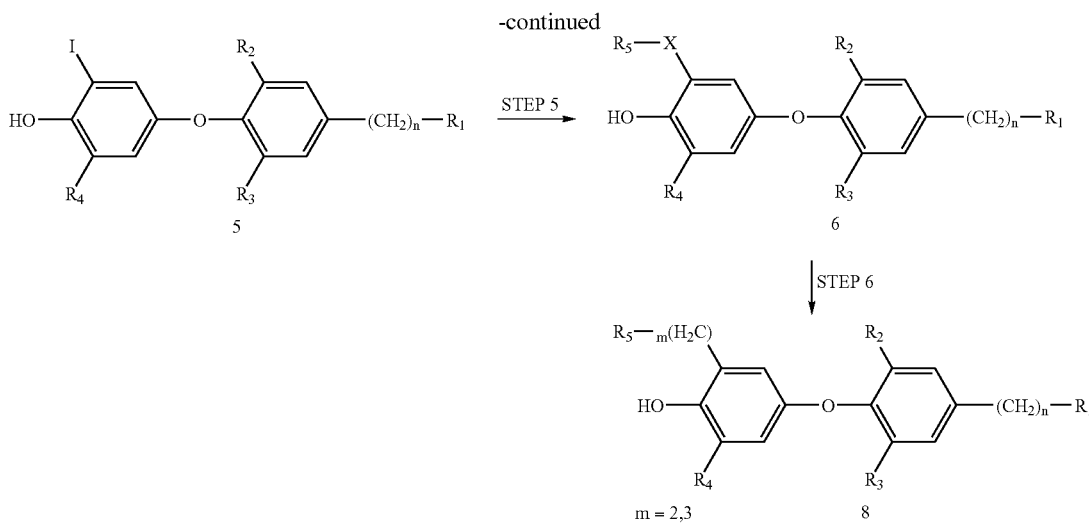

EXAMPLES

The following Examples represent preferred embodiments of the present invention. However, they should not be construed as limiting the invention in any way. The $^1$H NMR spectra were all consistent with the assigned structures in the Examples. Appropriate procedures for the preparation of methyl [3,5-dibromo-4-(4-methoxy-3-isopropylphenoxy)] benzoate and methyl [3,5-dibromo-4-(3-isopropyl-4-methoxyphenoxy)phenyl]propionate can be found in: "Novel Thyroid Receptor Ligands and Methods. Li, Yi-Lin; Liu, Ye; Hedfors, Asa; Malm, Johan; Mellin, Charlotta; Zhang, Minsheng. PCT Int. Appl., 40 pp. CODEN: PIXXD2. WO 9900353 A1 990107".

Example 1

3,5-Dibromo-4-[4-hydroxy-3-isopropyl-5-((E)-styryl)phenoxy]benzoic Acid (E1)

(a) Nitric acid (0.82 mL, 65%) was added dropwise to a well-stirred solution of methyl [3,5-dibromo-4-(3-isopropyl-4-methoxyphenoxy)]benzoate (2.0 mmol, 916 mg) in benzene (150 mL). The resulting reaction mixture was stirred at room temperature for one hour and then treated with saturated aqueous sodium hydrogencarbonate (10 mL). The organic phase was separated and the aqueous phase was extracted with chloroform (2×20 mL). The combined organic phases were concentrated and the residue was crystallized from aqueous ethanol (80%), to give 912 mg (91%) of methyl [3,5-dibromo-4-(5-isopropyl-4-methoxy-3-nitrophenoxy)]benzoate.

(b) A mixture of methyl [3,5-dibromo-4-(5-isopropyl-4-methoxy-3-nitrophenoxy)]benzoate (2.82 mmol, 1.42 g) and sodium dithionite ($Na_2S_2O_4$, 85% purity, 2.90 g, 14.1 mmol) in ethanol (150 mL, 95.5%) was stirred at 70° C. for 18 hours. The reaction mixture was concentrated, water (50 mL) and a saturated aqueous solution of sodium hydrogencarbonate solution (50 mL) was added to the residue. The mixture was extracted with ethyl acetate (5×25 mL), the combined organic extracts were washed with brine, dried over anhydrous sodium sulfate and concentrated. The residue was dissolved in diethyl ether (10 mL), iso-hexane (30 mL) was added and the mixture was cooled down to 0° C. The formed precipitate was filtered, collected and dried. This gave 1.23 g (92%) of methyl [3,5-dibromo-4-(3-amino-5-isopropyl-4-methoxyphenoxy)]benzoate.

(c) A solution of sodium nitrite (3.0 mmol, 207 mg) in water (5 mL) was added to a vigorously stirred mixture of methyl [3,5-dibromo-4-(3-amino-5-isopropyl-4-methoxy-phenoxy)]benzoate (2.0 mmol, 946 mg), methanol (40 mL) and hydrochloric acid (40 mL, 37%) at −15° C. The reaction mixture was stirred for one hour at the same temperature and then a solution of potassium iodide (6.0 mmol, 996 mg) in water (5 mL) was added. The reaction mixture was stirred for 30 minutes, while the temperature was kept between −15° C. and −10° C. The reaction mixture was extracted with chloroform (5×25 mL). The combined organic extracts were washed with an aqueous solution of saturated sodium hydrogencarbonate followed by a solution of sodium thiosulfate. The organic phase was dried over anhydrous sodium sulfate, filtered and concentrated. The residue was recrystallized from aqueous ethanol (80%), to give 874 mg (75%) of methyl [3,5-dibromo-4-(3-iodo-5-isopropyl-4-methoxyphenoxy)]benzoate.

(d) A mixture of methyl [3,5-dibromo-4-(3-iodo-5-isopropyl-4-methoxyphenoxy)]benzoate (0.685 mmol, 400 mg), potassium hydroxide (2 mL, 1 N) and ethanol (20 mL, 95.5%) was stirred at 70° C. for one hour. The reaction mixture was concentrated and the residue was acidified with hydrochloric acid (5 mL, 1 N). The aqueous phase was extracted with chloroform (5×10 mL), the combined organic phases were dried over anhydrous sodium sulfate and concentrated. This gave 3,5-dibromo-4-(3-iodo-5-isopropyl-4-methoxyphenoxy)benzoic acid which was used in the next step without further purification.
(e) Boron trifluoride dimethyl sulfide (13.7 mmol, 1.78 g) was added to a stirred solution of 3,5-dibromo-4-(3-iodo-5-isopropyl-4-methoxyphenoxy)benzoic acid in dichloromethane (50 mL). The resulting mixture was stirred at room temperature for 18 hours and then treated with water (30 mL). The organic phase was separated and the aqueous phase was extracted with chloroform (4×15 mL). The combined organic extracts were concentrated and treated with iso-hexane. The formed precipitate was filtered, dried and collected to give 345 mg (91%) of 3,5-dibromo-4-(4-hydroxy-3-iodo-5-isopropylphenoxy)benzoic acid.
(f) A mixture of 3,5-dibromo-4-(4-hydroxy-3-iodo-5-isopropylphenoxy)benzoic acid (0.060 mmol, 33 mg), styrene (0.18 mmol, 19 mg), trimethylbenzylammonium chloride (0.060 mmol, 11 mg), tris(dibenzylideneacetone)dipalladium (0.003 mmol, 3 mg), triethylamine (0.30 mmol, 30 mg) and dimethylformamide (4 mL) was placed in a Heck-vial and nitrogen was bubbled through the mixture for 5 minutes. The vial was closed hermetically and the mixture was stirred at 70° C. for 18 hours. The reaction mixture was concentrated, the residue acidified with an aqueous solution of hydrochloric acid (2 mL, 1 N) and extracted with chloroform (4×5 mL). The combined organic phases were concentrated and the residue was purified on a column (silica gel, chloroform/methanol 9:1) to give 14 mg (44%) of 3,5-dibromo-4-[4-hydroxy-3-isopropyl-5-((E)-styryl)phenoxy]benzoic acid. $^1$H NMR (CDCl$_3$) δ 1.20 (d, 6H, 2CH$_3$), 3.13 (sept., 1H, CH isopropyl), 4.80 (broad s, 1H, OH), 6.66 (s, 2H, H-2' and H-6'), 6.91 (d, 1H, CH double bond), 7.10-7.50 (m, 6H, 5H Ph and CH double bond), 8.32 (s, 2H, H-2 and H-6); LC-MS (ES) m/z 533 (M+1), 531 (M−1).

Example 2

3-{3,5-Dibromo-4-[4-hydroxy-3-isopropyl-5-((E)-styryl)phenoxy]phenyl}propionic Acid (E2)

(a) Methyl-3-[3,5-dibromo-4-(3-isopropyl-4-methoxyphenoxy)phenyl]propionate (2 mmol, 944 mg) was nitrated using the method described in Example 2(a) to give methyl-3-[3,5-dibromo-4-(5-isopropyl-4-methoxy-3-nitrophenoxy)phenyl]propionate. The crude product was used directly in the next step without further purification.
(b) Methyl-3-[3,5-dibromo-4-(3-isopropyl-4-methoxyphenoxy)phenyl]propionate was reduced using the method described in Example 2(b). The crude product was converted to its hydrochloric salt by the addition of a concentrated solution of hydrogen chloride in diethyl ether. After concentration of the reaction mixture the residue was dissolved in methanol and precipiated by the addition of diethyl ether and excess of iso-hexane. This gave 760 mg (71%/0) in two steps of methyl-3-(3,5-dibromo-4-(3-amino-5-isopropyl-4-methoxy-phenoxy)phenyl]propionate hydrochloride.
(c) Methyl-3-(3,5-dibromo-4-(3-amino-5-isopropyl-4-methoxyphenoxy)phenyl]propionate hydrochloride (6.23 mmol, 3.35 g) was diazotated using the method described in Example 2(c), to give 2.00 g (67%) of methyl-3-[3,5-dibromo-4-(3-iodo-5-isopropyl-4-methoxyphenoxy)phenyl]propionate.
(d) Methyl-3-[(3,5-dibromo-4-(3-iodo-5-isopropyl-4-methoxyphenoxy)phenyl]propionate (3.27 mmol, 2.00 g) was hydrolyzed using the method described in Example 2(d), to give 3-[(3,5-dibromo-4-(3-iodo-5-isopropyl-4-methoxyphenoxy)phenyl]propionic acid. The crude product was used in the next step without further purification.
(e) 3-[(3,5-Dibromo-4-(3-iodo-5-isopropyl-4-methoxyphenoxy)phenyl]propionic acid was demethylated using the method described in Example 2(e), to give 1.81 g (95% for steps 3(d) and 3(e)) of 3-[(3,5-dibromo-4-(4-hydroxy-3-iodo-5-isopropylphenoxy)phenyl]propionic acid.
(f) 3-[(3,5-dibromo-4-(4-hydroxy-3-iodo-5-isopropylphenoxy)phenyl]propionic acid (0.17 mmol, 99 mg) was coupled with styrene, using the method described in Example 2(f). This gave 71 mg (75%) of 3-{3,5-dibromo-4[4-hydroxy-5-isopropyl-3-(2-phenylvinyl)-phenoxy]phenyl}propionic acid. $^1$H NMR (CD$_3$COCD$_3$) δ 1.17 (d, 6H, J=6.9 Hz), 2.71 (t, 2H, J=7.4 Hz), 2.97 (t, 2H, J=7.4 Hz), 3.37 (m, 1H), 6.65 (d, 1H, J=3 Hz), 6.84 (d, 1H, J=3.0 Hz), 6.98 (d, 1H, 16.1 Hz), 7.24 (m, 1H), 7.33 (m, 2H), 7.51-7.57 (m, 3H), 7.67 (s, 2H); LC-MS (ES) m/z 561 (M+1), 559 (M−1).

Example 3

3-{3,5-Dibromo-4-[4-hydroxy-3-isopropyl-5-((E)-2-pyridin-4-yl-vinyl)-phenoxy]phenyl}propionic Acid (E3)

(a) To a stirred solution of methyl-3-[3,5-dibromo-4-(3-isopropyl-4-methoxyphenoxy)-phenyl]propionate (13.2 g, 27.1 mmol) in benzene (400 mL) at room temperature, nitric acid (16 mL, 65%) was added dropwise. After 4 hours at room temperature, an aqueous saturated solution of sodium bicarbonate was added until the pH of the reaction mixture was between 7 and 8. The organic phase was separated and the aqueous phase was extracted with chloroform (50 mL). The combined organic phases were concentrated and the residue purified twice on column (silica, n-heptane/ethyl acetate 4:1). This gave 10.7 g (74%) of methyl-3-[3,5-di-bromo-4-(3-isopropyl-4-methoxy-5-nitrophenoxy)phenyl]propionate.
(b) A mixture of methyl-3-[3,5-dibromo-4-(3-isopropyl-4-methoxy-5-nitrophenoxy)-phenyl]propionate (11.2 g, 21.1 mmol) and sodium dithionite (18.4 g, 105.7 mmol, 85% Na$_2$S$_2$O$_4$) in ethanol (800 mL, 95.5%) was stirred at 70° C. over night. The reaction mixture was concentrated and a saturated aqueous solution of sodium bicarbonate followed by ethyl acetate was added to the residue. The organic phase was washed once with brine, dried over magnesium sulphate, filtered and concentrated. The residue was purified on column (silica, heptane/ethyl acetate 3:2) to give 8.8 g (83%) of methyl 3-[3,5-dibromo-4-(3-amino-5-iso-propyl-4-methoxy)phenyl]propionate.
(c) To a vigorously stirred mixture of methyl 3-[3,5-dibromo-4-(3-amino-5-isopropyl-4-methoxy)phenyl]propionate (2.0 g, 4.0 mmol), methanol (100 mL) and hydrochloric acid (100 mL, 37%), sodium nitrite (417 mg, 6.0 mmol) in water (15 mL) was added drop-wise for 20 minutes, while keeping the temperature in the flask constant beetween −15 and −20° C. After 40 minutes, a solution of potassium iodide (3.8 g, 22.9 mmol) in water (15 mL) was added dropwise at −15° C. The reaction mixture was kept for 60 minutes at −15 to 0° C., and at 0 to 5° C. for an additional 60 minutes. The reaction mixture was extracted with chloroform (3×70 mL), the combined organic layers washed with a saturated aqueous solution of sodium hydrogencarbonate, then with saturated aqueous solution of sodium thiosulphate and finally with brine. The organic phase was dried over magnesium sulphate, filtered and concentrated, to give crude methyl-3-[3,5-dibromo-4-(3-iodo-5-isopropyl-4-methoxyphenoxy)phenyl]propionate (2.2 g, 92%). The compound was used directly in the next step.

(d) To a stirred solution of methyl-3-[3,5-dibromo-4-(3-iodo-5-isopropyl-4-methoxy-phenoxy)phenyl]propionate (2.1 g, 3.4 mmol) in dichloromethane (100 mL) was added boron trifluoride dimethyl sulfide (7.2 mL, 68.6 mmol) dropwise. The reaction mixture was stirred in the dark over night at room temperature. The mixture was carefully poured out over ice-water, the organic layer separated and the water phase extracted once with chloroform (50 mL). The combined organic phases were dried over magnesium sulphate and concentrated to give 2.0 g crude methyl-3-[3,5-dibromo-4-(4-hydroxy-3-iodo-5-isopropyl-phenoxy)-phenyl]propionate. The crude was used directly in the next step.

(e) To a solution of methyl-3-[3,5-dibromo-4-(4-hydroxy-3-iodo-5-isopropyl-phenoxy)-phenyl]propionate (586 mg, 0.98 mmol), and triethylamine (0.84 mL, 5.9 mmol) in dry dimethyl-formamide (15 mL), nitrogen gas was bubbled for 5 minutes, and then palladium(II) acetate (22.0 mg, 0.098 mmol) was added. After stirring for 5 minutes at room temperature, 4-vinyl-pyridine (618.1 mg, 5.9 mmol) was added and the reaction mixture heated at 100° C. over night. The reaction mixture was filtered through a pad of celite and the filtrate was concentrated. The residue was purified on column (silica, gradient of CHCl$_3$/CHOH from 98:2 to 95:5) to give 237 mg (42%) methyl-3-{3,5-dibromo-4-[4-hydroxy-3-isopropyl-5-((E)-2-pyridin-4-yl-vinyl)phenoxy]phenyl}propionate.

(f) To a stirred solution of methyl-3-{3,5-dibromo-4-[4-hydroxy-3-isopropyl-5-((E)-2-pyridin-4-yl-vinyl)phenoxy]phenyl}propionate (2.47 g, 4.3 mmol) in tetrahydrofuran (100 mL), lithium hydroxide (21.6 mL, 1 N) was added dropwise. After stirring over night at room temperature, the reaction mixture was concentrated, the residue taken with water and the pH adjusted to 7-8 with an aqueous solution of hydrochloric acid (2 N). Hot methanol was added to dissolve the precipitate, some water was removed in vacuo and on cooling a light yellow solid separated. The solid was filtrated and washed with cold water. Concentration of the mother liquor afforded another crop. After drying over phosphorous pentoxide under vacuum, 2.05 g (85%) of 3-{3,5-dibromo-4-[4-hydroxy-3-isopropyl-5-((E)-2-pyridin-4-yl-vinyl)-phenoxy]phenyl}propionic acid was obtained. $^1$H NMR (DMSO-d6) δ 1.07 (d, 6H, J=6.7), 2.26 (t, 2H, J=7.1), 2.80 (t, 2H, J=7.1), 3.31 (m, 1H), 6.53 (br d, 1H, J=2.7), 6.82 (br d, 1H, J=2.7), 6.95 (d, 1H, J=16.3), 7.50 (m, 2H), 7.60 (s, 2H), 7.84 (d, 1H, J=16.3 Hz), 8.48 (m, 2H); LC-MS (ES) m/z 559.9 (M−1).

Example 4

3-{3,5-Dibromo-4-[4-hydroxy-3-isopropyl-5-((E)-2-pyridin-2-yl-vinyl)-phenoxy]phenyl}propionic Acid (E4)

To a solution of methyl-3-[3,5-dibromo-4-(4-hydroxy-3-iodo-5-isopropyl)phenyl]propionate (15.5 mg, 0.026 mmol) in dry N,N-dimethylformamide (0.25 mL) was added a solution of 2-vinylpyridine (0.13 mmol) in dry N,N-dimethylformamide (0.25 mL) followed by triethylamine (0.018 mL, 0.13 mmol) and palladium(II) acetate (0.6 mg, 0.0026 mmol). The resulting reaction mixture was stirred at 100° C. for 16 hours and subsequently filtered through a celite plug. After concentration of the eluent in vacuo, the residue was purified on a silica SPE column (0.5 g/3 mL), eluting with a gradient mixture starting with n-heptane/ethyl acetate 99:1 and ending with a stronger eluent. The product containing fractions were collected, concentrated and the residue was dissolved in tetrahydrofuran (0.25 mL). LiOH (1N, 0.25 mL) was added and the resulting mixture was stirred at room temperature for 16 hours. The reaction mixture was then neutralised on an SCX (benzenesulphonic acid silane) SPE column (0.5 g/3 mL) using methanol or triethylamine (10% in methanol) as eluent. After concentration of the filtrate, the crude product was purified on a silica SPE column (0.5 g/3 mL) with a gradient starting with dichloromethane/methanol 99:1 and ending with a stronger eluent. The product containing fractions were collected and concentrated in vacuo yielding 1.11 mg (8.2%) of 3-{3,5-dibromo-4-[4-hydroxy-3-isopropyl-5-((E)-2-pyridin-2-yl-vinyl)phenoxy]phenyl}propionic acid. LC-MS (ES) m/z 560 (M−1).

Example 5

3-{3,5-Dibromo-4-[4-hydroxy-3-isopropyl-5-((E)-2-pyrazine-2-yl-vinyl)-phenoxy]phenyl}propionic Acid (E5)

2-Vinylpyrazine (0.13 mmol) was coupled with methyl-3-[3,5-dibromo-4-(4-hydroxy-3-iodo-5-isopropyl)phenyl]propionate (15.5 mg, 0.026 mmol) and subsequently deprotected using the procedure as described for Example 5. This gave 1.0 mg (6.8%) of 3-{3,5-dibromo-4-[4-hydroxy-3-isopropyl-5-((E)-2-pyrazine-2-yl-vinyl)phenoxy]phenyl}propionic acid. LC-MS (ES) m/z 561 (M−1).

Example 6

3-(3,5-Dibromo-4-{3-[(E)-2-(4-dimethylaminomethylphenyl)vinyl]-4-hydroxy-5-isopropylphenoxy}phenyl)propionic Acid (E6)

Dimethyl(4-vinylbenzyl)amine (0.13 mmol) was coupled with methyl-3-[3,5-dibromo-4-(4-hydroxy-3-iodo-5-isopropyl)phenyl]propionate (15.5 mg, 0.026 mmol) and subsequently deprotected using the procedure as described for Example 5. This gave 0.47 mg (2.9%) of 3-(3,5-dibromo-4-(3-[(E)-2-(4-dimethylaminomethylphenyl)vinyl]-4-hydroxy-5-isopropyl-phenoxyphenyl)propionic acid. LC-MS (ES) m/z 616 (M−1).

Example 7

3-(3,5-Dibromo-4-{4-hydroxy-3-isopropyl-5-[(E)-2-(4-methylthiazol-5-yl)-vinyl]phenoxy}phenyl)propionic Acid (E7)

5-Vinyl-4-methylthiazol (0.13 mmol) was coupled with methyl-3-[3,5-dibromo-4-(4-hydroxy-3-iodo-5-isopropyl)phenyl]propionate (15.5 mg, 0.026 mmol) and subsequently deprotected using the procedure as described for Example 5. This gave 2.6 mg (17%) of 3-(3,5-dibromo-4-{4-hydroxy-3-isopropyl-5-[(E)-2-(4-methylthiazol-5-yl)vinyl]phenoxyphenyl)propionic acid. LC-MS (ES) m/z 580 (M−1).

Example 8

4-((E)-2-{5-[2,6-Dibromo-4-(2-carboxyethyl)phenoxy]-2-hydroxy-3-iso-propylphenyl}vinyl)benzoic Acid (E8)

4-Vinylbenzoic acid (0.13 mmol) was coupled with methyl-3-[3,5-dibromo-4-(4-hydroxy-3-iodo-5-isopropyl)phenyl]propionate (15.5 mg, 0.026 mmol) and subsequently deprotected using the procedure as described for Example 5. This gave 2.4 mg (15%) of 4-((E)-2-{5-[2,6-dibromo-4-(2-carboxyethyl)phenoxy]-2-hydroxy-3-isopropylphenyl}-vinyl)benzoic acid. LC-MS (ES) m/z 603 (M−1).

Example 9

3-[3,5-Dibromo-4-4-hydroxy-3-isopropyl-5-(2-pyridin-4-yl-ethyl)-phenoxy]-phenyl}propionic Acid (E9)

(a) To a solution of methyl{3,5-dibromo-4-[4-hydroxy-3-isopropyl-5((E)-2-pyridin-4-yl-vinyl)-phenoxy]-phenyl}propionate prepared according to the procedure described in Example 4(e) (204 mg, 0.35 mmol) in ethyl acetate (12 mL) was added PtO$_2$ (8 mg, 0.04 mmol). The reaction was hydrogenated at room temperature (1 atm.) overnight. Flash chromatography (hexane/EtOAc 50:50-30:70) afforded 130 mg (64%) of methyl 3-f{3,5-dibromo-4-[4-hydroxy-3-isopropyl-5-(2-pyridinyl-ethyl)-phenoxy]-phenyl}propionate as a light yellow solid.

(b) To a stirred solution of methyl 3-{3,5-dibromo-4-[4-hydroxy-3-isopropyl-5-(2-pyridin-4-yl-ethyl)-phenoxy]-phenyl}propionate (125 mg, 0.22 mmol) in THF (5 mL), lithium hydroxide (1 mL, 1N) was added dropwise. The reaction was stirred at room temperature for 2.5 h. After concentration, water (5 mL) was added and the pH adjusted to 7 with 1 M HCl (aq). The thus precipitated solid was filtered, washed with cold water and dried to give 95 mg (77%) of -{3,5-dibromo-4-[4-hydroxy-3-isopropyl-5-2-pyridin-4-yl-ethyl)-phenoxy]-phenyl}propionic acid as a light yellow solid. $^1$H NMR (CD$_3$OD): δ 1.20 (d, 6H), 2.70 (m, 2H), 2.95 (br s, 6H), 3.30 (m, 1H), 6.05 (s, 1H), 6.60 (s, 1H), 7.20 (br s, 2H), 7.60 s, 2H), 8.30 (br s, 2H). MS (ES): m/z 564 (M+1).

Example 10

3-[3,5-Dibromo-4-(4-hydroxy-3-isopropyl-5-phenetyl-phenoxy)-phenyl]propionic Acid (E10)

(a) A solution of methyl 3-[3,5-dibromo-4-(4-hydroxy-3-iodo-5-isopropyl-phenoxy)-phenyl]propionate prepared according to the procedure described in Example 4(d) (500 mg, 0.84 mmol), diisopropylethyl amine (320 mg, 2.48 mmol) and lithium chloride (40 mg; 0.94 mmol) in dry DMF (15 mL) was degassed with nitrogen for 5 minutes, followed by the addition of palladium(II)acetate (19 mg, 0.08 mmol). After stirring for 5 min. at room temperature, styrene (260 mg, 2.50 mmol) was added by syringe and the reaction mixture heated at 75° C. overnight. The reaction mixture was evaporated to dryness and purified by flash chromatography (hexane/EtOAc 80:20) to give 450 mg (94%) methyl 3-[3,5-dibromo-4-(4-hydroxy-3-isopropyl-5-((E)-styryl)-phenoxy)-phenyl]propionate.

(b) To a solution of methyl 3-[3,5-dibromo-4-(4-hydroxy-3-isopropyl-5((E)-styryl)-phenoxy)-phenyl]propionate (160 mg, 0.28 mmol) in ethyl acetate (6 mL) was added PtO$_2$ (8 mg, 0.04 mmol). The reaction mixture was hydrogenated at room temperature (1 atm.) overnight, filtered and concentrated. The crude product was hydrolysed directly in the next step.

(c) To a stirred solution of methyl 3-[3,5-dibromo-4-(4-hydroxy-3-isopropyl-5-phenethyl-phenoxy)-phenyl]propionate (150 mg, 0.26 mmol) in THF (5 mL), lithium hydroxide (1 mL, 1N) was added dropwise. The reaction was stirred at room temperature for 4 hours. After concentration, water (5 mL) was added and the pH adjusted to 7 with 1 M HCl (aq). The crude was concentrated to dryness and purified by flash chromatography (hexane/EtOAc 50:50) to afford 102 mg (65%, two steps) 3-[3,5-dibromo-4-(4-hydroxy-3-isopropyl-5-phenethyl-phenoxy)-phenyl]propionic acid. $^1$H NMR (CD$_3$OD): δ (d, 6H), 2.64 (t, 2H), 2.81-2.94 (m, 6H), 3.30 (m, 1H), 6.14 (d, 1H), 6.48 (d, 1H), 7.07-7.22 (m, 5H), 7.52 (s, 2H). MS (ES): m/z 563 (M+1).

Example 11

3-[3,5-Dibromo-4-[4-hydroxy-3-isopropyl-5(E)-styryl-phenoxy)phenyl]-2-hydroxy-propionic Acid (E11)

(a) To a suspension of bis(3-isopropyl-4-methoxyphenyl)iodonium tetrafluorborate (5.75 g; 11.3 mmol) and copper bronze (1 g) in dichloromethane (30 mL) was added a solution of methyl 3,5-dibromo-4-hydroxy benzoate (2.5 g, 7.1 mmol) and triethylamine (1.2 mL) in dichloromethane (20 mL) slowly at room temperature. The mixture was stirred overnight, evaporated to dryness and subjected to flash chromatography (Hexane/EtOAc 9:1 followed by hexane/EtOAc 6:4) affording 3.35 g (94%) of methyl 3-[3,5-dibromo-4-(3-isopropyl-4-methoxy-phenoxy)-phenyl]-2-hydroxy-propionate as a white solid.

(b) To a stirred solution of methyl 3-[3,5-bromo-4(3-isopropyl methoxy-phenoxy)-phenyl]-2-hydroxy-propionate (3.15 g, 6.3 mmol) in benzene (95 mL) at room temperature, nitric acid (3.7 mL, 65%) was added drop-wise. After stirring overnight the pH of the reaction mixture was adjusted to 7 with saturated sodium bicarbonate. The organic phase was separated and the aqueous phase extracted with dichloromethane (2×50 mL). The combined organic extracts were concentrated and the residue purified with flash chromatography (CH$_2$Cl$_2$/MeOH 99:1) affording methyl 3-[3,5-dibromo-4-(3-isopropyl-4-methoxy-5-nitro-phenoxy)-phenyl]-2-hydroxy-propionate in quantitative yield as a yellow solid.

(c) To a solution of methyl 3-[3,5-dibromo-4-(3-isopropyl-4-methoxy-5-nitro-phenoxy)phenyl]-2-hydroxy-propionate (3.4 g; 6.2 mmol) in ethanol (235 mL) was added sodium dithionite (5.5 g). The reaction mixture was stirred at 70° C. overnight. The reaction mixture was concentrated and a saturated aqueous solution of sodium bicarbonate (100 mL) was added to the residue. Extraction with EtOAc (2×100 mL), washing of the organic extracts with brine (100 mL), drying (MgSO$_4$), filtering and concentration gave a residue which was purified by flash chromatography (CH$_2$Cl$_2$/MeOH 99:1 followed by CH$_2$Cl$_2$/MeOH 75:25 giving 2.75 g (86%) of methyl 3-[4-(3-amino-5-isopropyl-4-methoxy-phenoxy)-3,5-dibromo-phenyl]-2-hydroxy-propionate.

(d) To a vigorously stirred mixture of methyl 3-[4-(3-amino-5-isopropyl-4-methoxy-phenoxy)-3,5-dibromo-phenyl]-2-hydroxy-propionate (2.15 g, 4.15 mmol), methanol (100 mL) and an aqueous solution of hydrochloric acid (100 mL, 37%), sodium nitrite (0.43 g, 6.3 mmol) in water (20 mL) was added dropwise for 20 min. while keeping the temperature in the reaction flask between −15 and −20° C. After 40 min, a solution of potassium iodide (3.9 g; 23.5 mmol) in water (15 mL) was added slowly at −15° C. The reaction mixture was kept for 60 min. at −15 to 0° C., and at 0 to 5° C. for an additional hour. The reaction mixture was extracted with dichloromethane (3×100 mL), the combined organic extracts washed with saturated sodium bicarbonate (150 mL), saturated sodium thiosulphate (100 mL) and with brine (150 mL). After drying (MgSO$_4$), filtration and concentration the crude product was subjected to flash chromatography (CH$_2$Cl$_2$/MeOH 99:1) to give 1.5 g methyl 3-[3,5-dibromo-4-(3-iodo-5-isopropyl-4-methoxy-phenoxy)-phenyl]-2-hydroxy-propionate as a brown oil.

(e) To a stirred solution of methyl 3-[3,5-dibromo-4-(3-iodo-5-isopropyl-4-methoxy-phenoxy)-phenyl]-2-hydroxy-propionate (1.95 g, 3.1 mmol) in dichloromethane (90 mL) was added boron trifluoride dimethyl sulfide (6.6 mL) slowly at room temperature. The reaction mixture was left stirring overnight in the dark. The reaction mixture was carefully poured over ice-water, the organic layer separated and the water layer extracted with dichloromethane. The combined organic phases were dried over magnesium sulphate, filtered and evaporated to dryness. The crude product was dissolved in methanol (7 mL), concentrated hydrochloric acid was added (12 N, 0.19 mL) and the mixture was stirred for 20 hours at room temperature. After concentration of the reaction mixture, the residue was dissolved in ethyl acetate (50 mL) and washed with a saturated aqueous solution of sodium bicarbonate (20 mL). The aqueous layer was extracted with dichloromethane (30 mL) and the combined organic layers were washed with saturated brine (40 mL), dried (MgSO$_4$), filtered and concentrated in vacuo. Flash chromatography (hexane/EtOAc 70:30) on silica gel afforded 1.47 g (77%) of methyl 3-[3,5-dibromo-4-(4-hydroxy-3-iodo-5-isopropyl-phenoxy)-phenyl]-2-hydroxy-propionate as a brown oil. The compound was further purified by recrystallization from a mixture of EtOAC, CH$_2$Cl$_2$ and hexane affording approximately 80% of the material obtained from flash chromatography as a white solid.

(f) A solution of methyl 3-[3,5-dibromo-4-(4-hydroxy-3-iodo-5-isopropyl-phenoxy)-phenyl]-2-hydroxy-propionate (380 mg, 0.62 mmol), diisopropylethyl amine (0.32 mL, 1.86 mmol) and lithium chloride (26 mg, 0.62 mmol) in dry DMF (6 mL), was degassed with nitrogen gas for 5 minutes, followed by addition of palladium(II)acetate (29 mg, 0.13 mmol). After stirring for 5 min. at room temperature, styrene (0.21 mL, 1.86 mmol) was added by syringe and the reaction mixture heated at 80° C. overnight. The reaction mixture was evaporated to dryness and purified by flash chromatography (hexane/EtOAc 70:30) to give 350 mg (96%) of methyl 3-[3,5-dibromo-4-(4-hydroxy-3-isopropyl-5-((E)-styryl)-phenoxy)-phenyl]-2-hydroxy-propionate as a colourless oil.

(g) To a solution of methyl 3-[3,5-dibromo-4-(4-hydroxy-3-isopropyl-5-((E)-styryl)-phenoxy)-phenyl]-2-hydroxy-propionate (80 mg, 0.14 mmol) in THF (3 mL) was added lithium hydroxide (0.7 mL, 1N). The mixture was vigorously stirred for 1 hour at room temperature, then concentrated in vacuo. The residue was dissolved in water (2 mL) and the pH adjusted to 7 with 1 M HCl. The precipitate was collected by filtration, washed with H$_2$O and dried to afford 3-[3,5-dibromo-4-(4-hydroxy-3-isopropyl-5-((E)-styryl)-phenoxy)-phenyl]-2-hydroxy-propionic acid (30 mg, 38%) as a colourless solid. $^1$H NMR (CD$_3$OD) δ 1.2 (d, 6H), 2.9-3.1(m, 3H), 4.4 (m, 1H), 6.6(d, 1H), 6.7 (d, 1H), 6.9 (d, 1H), 7.2-7.3 (m, 3H); 7.4-7.5 (m, 3H); 7.6 (s, 2H). MS (ES) m/z 575 (M−1)

Example 12

3-{3,5-Dibromo-4-[4-hydroxy-3-isopropyl-5-((E)-2-pyridin-4-yl-vinyl)-phenoxy]-phenyl}-2-hydroxy Propionic Acid (E12)

(a) A solution of methyl 3-[3,5-dibromo-4-(3-iodo-5-isopropyl-4-hydroxy-phenoxy)-phenyl]-2-hydroxy-propionate prepared according to the procedure described in Example 12(e) (380 mg, 0.62 mmol), diisopropylethyl amine (0.32 mL, 1.86 mmol) and lithium chloride (26 mg, 0.62 mmol) in dry DMF (6 mL), was degassed with nitrogen gas for 5 minutes, followed by addition of palladium(II)acetate (29 mg, 0.13 mmol). After stirring for 5 min. at room temperature, 4-vinyl-pyridine (0.21 mL, 1.97 mmol) was added by syringe and the reaction mixture heated at 80° C. overnight. The reaction mixture was evaporated to dryness and purified twice by flash chromatography (CH$_2$Cl$_2$ followed by CH$_2$Cl$_2$/MeOH 75:25 and CH$_2$Cl$_2$: MeOH 19:1) to give 230 mg (63%) of methyl 3-{3,5-dibromo-4-[4-hydroxy-3-isopropyl-5-((E)-2-pyridin-4-yl-vinyl)-phenoxy]-phenyl}-2-hydroxy-propionate as a yellow solid.

(b) To a solution of methyl 3-{3,5-dibromo-4-[4-hydroxy-3-isopropyl-5-((E)-2-pyridin-4-yl-vinyl)-phenoxy]-phenyl}-2-hydroxy-propionate (60 mg, 0.1 mmol) in THF (2 mL) was added lithium hydroxide (0.5 mL, 1N). The mixture was vigorously stirred for 1 hour at room temperature, then concentrated in vacuo. The residue was dissolved in water (2 mL) and the pH adjusted to 7 with 1 M HCl. The precipitate was collected by filtration, washed with H$_2$O and dried to afford 3-{3,5-dibromo-4-[4-hydroxy-3-isopropyl-5((E)-2-pyridin-4-yl-vinyl)-phenoxy]-phenyl}-2-hydroxy-propionic acid (50 mg, 86%) as a yellow solid. $^1$H NMR (DMSO-d6) δ 1.1 (d, 6H), 2.8-3.4 (m, 3H), 4.3 (m, 1H), 6.6 (d, 1H), 6.8 (d, 1H), 7.0 (d, 1H), 7.5 (d, 2H), 7.7 (s, 2H), 7.8 (d, 1H), 8.6 (d, 2H), 8.7 (br s, 1H). MS (ES) m/z 622 (M+2Na).

Example 13

3-[3,5-Dibromo-4-(4-hydroxy-3-isopropyl-5-phenyl-ethyl-phenoxy)-phenyl]-2-hydroxy-propionic Acid (E13)

(a) To a solution of methyl 3-[3,5-dibromo-4-(4-hydroxy-3-isopropyl-5-((E)-styryl)-phenoxy)-phenyl]-2-hydroxy-propionate (136 mg, 0.23 mmol) prepared according to the procedure described in Example 12(f) in MeOH (2 mL) was added PtO$_2$ (13 mg; 0.06 mmol) and the mixture was stirred vigorously under hydrogen gas (1 atm.) for 20 hours. The mixture was filtered and the resulting solution concentrated in vacuo. Flash chromatography of the residue on silica gel (hexane/EtOAc 6:4) afforded 126 mg (92%) of methyl 3-[3,5-dibromo-4-(4-hydroxy-3-isopropyl-5-phenylethyl-phenoxy)-phenyl]-2-hydroxy-propionate as a colourless oil.

(b) To a solution of methyl 3-[3,5-dibromo-4-(4-hydroxy-3-isopropyl-5-phenylethyl-phenoxy)-phenyl]-2-hydroxy-propionate (117 mg, 0.2 mmol) in THF (2 mL) was added lithium hydroxide (1 mL, 1N). The mixture was vigorously stirred for 1 hour at room temperature, then concentrated in vacuo. The residue was dissolved in water (2 mL) and the pH adjusted to 7 with 1 M HCl. The precipitate was collected by filtration, washed with H$_2$O and dried to afford 3-[3,5-dibromo-4-hydroxy-3-isopropyl-5-phenylethyl-phenoxy)-phenyl]-2-hydroxy-propionic acid (39 mg, 34%) as a colourless solid. $^1$H NMR (CD$_3$OD) d 1.1 (d, 6H), 2.6-3.2 (m, 31, 2.8 (br s, 4H), 4.2 (m, 1H), 6.2 (d, 1H), 6.5 (d, 1H), 7. -7.3 (m, 5H), 7.7 (s, 2H). MS (ES): m/z 623 (M+2Na).

Example 14

3-{3,5-Dibromo-4-[4-hydroxy-3-isopropyl-5-(2-pyridin-4-yl-ethyl)-phenoxy]-phenyl}-2-hydroxy-propionic Acid (E14)

(a) To a solution of methyl 3-{3,5-dibromo-4-[4-hydroxy-3-isopropyl-5((E)-2-pyridin-4-yl-vinyl)-phenoxy]-phenyl}-2-hydroxy-propionate prepared according to the procedure described in Example 13a (112 mg, 0.19 mmol) in MeOH (2 mL) was added $PtO_2$ (11 mg, 0.05 mmol) and the mixture was stirred vigorously under hydrogen gas (1 atmosphere) for 20 hours. The mixture was filtered and the resulting solution concentrated in vacuo. Flash chromatography of the residue ($CH_2Cl_2$/MeOH 95:5) afforded 47 mg (42%) of methyl 3-{3,5-dibromo-4-[4-hydroxy-3-isopropyl-5-(2-pyridin-4-yl-ethyl)-phenoxy]-phenyl}-2-hydroxy-propionate as a colourless oil.

(b) To a solution of methyl 3-{3,5-dibromo-4-[4-hydroxy-3-isopropyl-5-(2-pyridin-4-yl-ethyl)-phenoxy]-phenyl}-2-hydroxy-propionate (47 mg, 0.08 mmol) in THF (2 mL) was added lithium hydroxide (0.4 mL, 1N). The mixture was vigorously stirred for 1 hour at room temperature, then concentrated in vacuo. The residue was dissolved in water (2 mL) and the pH adjusted to 7 with 1 M HCl. The precipitate was collected by filtration, washed with $H_2O$ and dried to afford 3-{3,5-dibromo-4-[4-hydroxy-3-isopropyl-5-(2-pyridin-4-yl-ethyl)-phenoxy]-phenyl}-2-hydroxy-propionic acid (36 mg, 78%) as a yellow solid $^1$H NMR (DMSO-d6) d 1.1 (d, 6H), 2.8 (m, 4H), 3.0 (dd, 2H), 3.3 (m, 1H); 4.1 (m, 1H), 6.2 (d, 1H), 6.5 (d, 1H), 7.2 (d, 2H), 7.4 (s, 1H), 7.6 (s, 2H), 8.0 (br s, 1H), 8.4 (d, 2H). MS (ES): m/z 624 (M+2Na).

The compounds of the invention exhibit binding affinities to the ThRα receptor in the range of 10 to 500 nM.

The invention claimed is:

1. A compound according to the general formula:

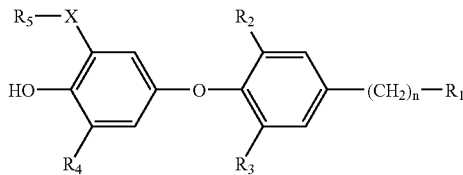

or a pharmaceutically acceptable salt thereof, wherein:
$R_1$ is independently selected from: carboxylic acid (—$CO_2H$); carboxylic acid ester (—$CO_2R^c$); alpha-hydroxy carboxylic acid (—CH(OH)$CO_2H$); alpha-amino carboxylic acid (—CH($NH_2$)$CO_2H$); phosphonic acid (—PO(OH)$_2$); phosphamic acid (—PO(OH)$NH_2$); sulphonic acid (—$SO_2OH$); hydroxamic acid (—CONHOH); oxamic acid (—NHCO$CO_2H$); and malonamic acid (—NHCO$CH_2CO_2H$), and bioisosteric equivalents of any thereof;
$R_2$ and $R_3$ are the same or different and independently selected from: chlorine; bromine; iodine; $C_{1-4}$ alkyl or haloalkyl; $C_{2-4}$ alkenyl or haloalkenyl; $C_{2-4}$ alkynyl or haloalkynyl, or a bioisosteric equivalent of any thereof;
$R_4$ is selected from: halogen; $C_{1-4}$ alkyl; $C_{2-4}$ alkenyl; and $C_{2-4}$ alkynyl, each being optionally substituted with 1, 2 or 3 halogen atoms, which may be the same or different, or a bioisosteric equivalent of any thereof;
X is selected from: —$CH_2$—$CH_2$—; —$CH_2$—$CH_2$—$CH_2$; —CH=CH—; —CH=CH—$CH_2$—; —C≡C—; and —C≡C—$CH_2$;
$R_5$ is selected from $C_{6-10}$ aryl; $C_{1-9}$ heteroaryl; and $C_{5-10}$ cycloalkyl, each being optionally substituted with 1, 2, or 3 groups of $R^b$ which may be the same or different;
$R^b$ is selected from: halogen; —CN; —$CO_2H$; —CHO; —$NO_2$; $C_{1-4}$ alkyl; $C_{2-4}$ aklenyl; $C_{2-4}$ alkynyl; $C_{1-4}$ alkoxy; $C_{2-4}$ alkenoxy; $C_{2-4}$ alkynoxy; $C_{1-4}$ alkylthio; $C_{2-4}$ alkenylthio; $C_{2-4}$ alkynylthio; —(CH$_2$)$_n$—OH; —(CH$_2$)$_n$—O($C_{1-4}$); —(CH$_2$)$_n$—$NH_2$; —(CH$_2$)$_n$—NH($C_{1-4}$); and —(CH$_2$)$_n$—N($C_{1-4}$)$_2$, or a bioisosteric equivalent of any thereof;
$R^c$ is selected from $C_{1-4}$ alkyl; $C_{2-4}$ alkenyl; and $C_{2-4}$ alkynyl;
n is 1 or 2;
and prodrug ester forms thereof.

2. A compound according to claim 1 wherein $R_1$ is selected from: carboxylic acid (—$CO_2H$); alpha-hydroxy carboxylic acid (—CH(OH)$CO_2H$); and alpha-amino carboxylic acid (—CH($NH_2$)$CO_2H$).

3. A compound according to claim 1 wherein $R_3$ is bromine.

4. A compound according to claim 1 wherein $R_4$ is isopropyl.

5. A compound according to claim 1 wherein $R_5$ is $C_6$ aryl or $C_{1-5}$ heteroaryl.

6. A compound according to claim 1 wherein $R_1$ is a carboxylic acid (—$CO_2H$); $R_2$ and $R_3$ is bromine; $R_4$ is isopropyl; $R_5$ is $C_6$ aryl or $C_{1-5}$ heteroaryl.

7. A compound according to claim 1 which is:
3,5-dibromo-4-[4-hydroxy-3-isopropyl-5-((E)-styryl)phenoxy]benzoic acid (E1);
3-{3,5-dibromo-4-[4-hydroxy-3-isopropyl-5((E)-styryl)phenoxy]phenylpropionic acid (E2);
3-{3,5-dibromo-4-[4-hydroxy-3-isopropyl-5((E)-2-pyridin-4-yl-vinyl)phenoxy]-phenyl propionic acid (E3);
3-{3,5-dibromo-4-[4-hydroxy-3-isopropyl-5((E)-2-pyridin-2-yl-vinyl)phenoxy]phenyl}-propionic acid (E4);
3-{3,5-dibromo-4-[4-hydroxy-3-isopropyl-5-((E)-2-pyrazine-2-yl-vinyl)phenoxy]phenyl}-propionic acid (E5);
3-(3,5-dibromo-4-{3-[(E)-2-(4-dimethylaminomethylphenyl)vinyl]-4-hydroxy-5-isopropyl phenoxy}phenyl)propionic acid (E6);
3-(3,5-Dibromo-4-{4-hydroxy-3-isopropyl-5-[(E)-2-(4-methylthiazol-5-yl)vinyl]phenoxy}-phenyl)propionic acid (E7);
4-((E)-2-{5-[2,6-Dibromo-4-(2-carboxyethyl)phenoxy]-2-hydroxy-3-isopropylphenylvinyl)-benzoic acid (E8);
3-{3,5-Dibromo-4-[4-hydroxy-3-isopropyl-5-(2-pyridin-4-yl-ethyl)-phenoxy]-phenyl}propionic acid (E9);
3-[3,5-Dibromo-4-(4-hydroxy-3-isopropyl-5-phenetyl-phenoxy)-phenyl]-propionic acid (E10);
3-[3,5-Dibromo-4-[4-hydroxy-3-isopropyl-5(E)-styryl-phenoxy)phenyl]-2-hydroxy propionic acid (E11);
3-{3,5-Dibromo-4-[4-hydroxy-3-isopropyl-5-((E)-2-pyridin-4-yl-vinyl)-phenoxy]-phenyl}-2-hydroxy propionic acid (E12);
3-[3,5-Dibromo-4-[4-hydroxy-3-isopropyl-5-phenylethyl-phenoxy)-phenyl]-2-hydroxy-propionic acid (E13);
3-{3,5-Dibromo-4-[4-hydroxy-3-isopropyl-5-(2-pyridin-4-yl-ethyl)-phenoxy]-phenyl}-2-hydroxy propionic acid (E14);
and pharmaceutically acceptable salts thereof.

8. A pharmaceutical composition comprising an effective amount of a compound according to claim 1 or a pharmaceutically effective salt thereof, together with a pharmaceutically acceptable carrier.

* * * * *